United States Patent [19]

Mathew

[11] Patent Number: 5,021,587

[45] Date of Patent: Jun. 4, 1991

[54] SYNTHESIS OF N,3,4-TRISUBSTITUTED-3-AZOLINE-2-ONES

[75] Inventor: Jacob Mathew, Fenton, Mo.

[73] Assignee: Petrolite Corporation, St. Louis, Mo.

[21] Appl. No.: 469,657

[22] Filed: Jan. 24, 1990

[51] Int. Cl.$^5$ ............................................. C07D 207/38
[52] U.S. Cl. ................................................... 548/543
[58] Field of Search .......................................... 548/543

[56] References Cited

U.S. PATENT DOCUMENTS 3,272,842  9/1966  Easton et al. ..................... 260/326.5
3,452,015  6/1969  Dillard et al. ........................ 548/554

FOREIGN PATENT DOCUMENTS 1073944  7/1967  United Kingdom .
2028307A  3/1980  United Kingdom .

*Primary Examiner*—David B. Springer
*Attorney, Agent, or Firm*—Jeffrey S. Boone

[57] ABSTRACT

N,3,4-trisubstituted-3-azoline-2-ones (such as N-benzyl-3,4-dimethyl-3-azoline-2-one) are prepared by the reaction of an alkyl 2-chloro-2,3-disubstituted-3-butenoate (such as ethyl 2-chloro-2,3-dimethyl-3-butenoate) with a primary amine (such as benzyl amine). Methods for preparing the precursor esters are also disclosed.

14 Claims, No Drawings

SYNTHESIS OF N,3,4-TRISUBSTITUTED-3-AZOLINE-2-ONES

BACKGROUND OF THE INVENTION

This invention relates to the synthesis of cyclic nitrogen compounds. In particular, the invention relates to the synthesis of N,3,4-trisubstituted-3-azoline-2-ones, (also known as 1,5-dihydro-1,5,N-trisubstituted-2-H-pyrol-2-ones).

N,3,4-trisubstituted-3-azoline-2-ones are useful as central nervous system drugs and as pharmaceutical intermediates.

U.S. Pat. No. 3,272,842 (Easton - Eli Lilly, 1966) describes the synthesis of related compounds by the cyclization of N-acyl derivatives of β-keto amines in the presence of a strong base in a solvent.

GB 2,028,307 (Hofer - Mundipharma, 1980) teaches the synthesis of related compounds by the ring closure of an N-aroylmethyl acetamide in basic media under nitrogen.

SUMMARY OF THE INVENTION

Briefly, the invention comprises a method of preparing an N,3,4-trisubstituted-3-azoline-2-one by reacting together
(a) an alkyl 2-chloro-2,3-disubstituted-3-butenoate with
(b) a primary amine.

The method of the invention is particularly economical and simple to carry out.

DETAILED DESCRIPTION OF THE INVENTION

In this specification and claims, numerical values are not critical unless otherwise stated. That is, the numerical values may be read as if they were prefaced with the word "about" or "substantially".

A first compound used in the process of the invention is an alkyl 2-chloro-2,3-disubstituted-3-butenoate. Such compounds have the general formula:

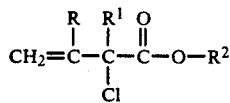

wherein R and $R^1$ are each independently H or organic moieties; generally H or hydrocarbon moieties; desirably H, aryl, or alkyl; more desirably H, $C_6$ to $C_{32}$ aryl, or $C_1$ to $C_{32}$ alkyl; preferably H, $C_6$ to $C_{16}$ aryl, or $C_1$ to $C_{16}$ alkyl; and more preferably H, $C_6$ aryl, or $C_1$ to $C_6$ alkyl; and $R^2$ is an alkyl, desirably a $C_1$ to $C_{12}$ alkyl, preferably a $C_1$ to $C_6$ alkyl, and most preferably a $C_2$ alkyl moiety.

Alkyl 2-chloro-2,3-disubstituted-3-butenoates may be conveniently prepared by the reaction of an alkyl 2,3-disubstituted-2-butenoate of the formula:

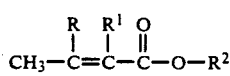

wherein R, $R^1$, and $R^2$ are as defined above, with Ca(OCl)$_2$ and ethanoic acid in a two phase system of water and dichloromethane, generally following the method of Wolinsky and coauthors in Tetrahedron Lett., 1981, 5019; and Tetrahedron Lett., 1980, 441;both of which are incorporated herein by reference.

Another method of preparing alkyl 2-chloro-2,3-disubstituted-3-butenoates is to react a 2-chloro-3-substituted-3-butenoate,

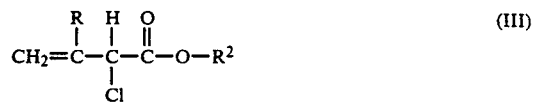

with an alkylating agent such as an alkyl halide or an alkyl tosylate, in the presence of a solvent such as tetrahydrofuran and a base such as potassium hexamethyldisilazide KN[Si(CH$_3$)$_3$]$_2$ In each case, the alkyl moiety replaced the hydrogen on the 2-carbon.

A second compound useful in the practice of the invention is a primary amine. The primary amine can be virtually any primary amine and may be represented by the general formula:

wherein $R^3$ is H or an organic group such as alkyl, cycloalkyl, or aryl. Preferred $R^3$ moieties include benzyl.

The reaction of the ester and the amine desirably takes place in solvent such as toluene and at temperatures of 0° C. to 120° C., preferably 20° C. to 100° C. The products of the invention have the structure:

in which R, $R^1$, and $R^3$ are as defined above. The products may be separated from the reaction mixture by low temperature methods such as crystallization or flash column chromatography. The products of the invention have utility in applications such as central nervous system regulators and pharmaceutical intermediates.

The invention will be further explained in the following examples. In the examples, all parts and percentages are by weight unless otherwise specified.

EXAMPLE 1

(Precursor, method i)

14 g (0.1 mole) of ethyl 2,3-dimethyl-2-butenoate was added in a single portion to a stirred suspension of 11 g (70 millimole) calcium hypochlorite in 20 ml of dichloromethane. The mixture was cooled to 0° C. and 50 ml of water was added, followed by rapid addition of 8 ml (0.14 mole) of glacial acetic acid. The cloudy, two-phase system was stirred in an ice bath for 15 minutes and then warmed to room temperature. 100 ml water and 200 ml dichloromethane were added, and the organic layer was isolated, washed with dilute sodium bicarbonate (2×40 ml), washed with water (40 ml), and then dried over anhydrous magnesium sulfate. Evaporation of solvents yielded 15 g of a colorless oil. Gas chromatography and gas chromatograph/mass spectroscopy indicated that the oil was 90% ethyl 2-chloro-2,3-dimethyl-3-butenoate, (Formula I, R=CH$_3$, $R^1$=CH$_3$).

EXAMPLE 2

(Precursor, method i)

Generally following the procedures of Example 1, the E-isomer of ethyl 2-methyl-3-phenyl-2-butenoate was used to produce ethyl 2-chloro-2-methyl-3-phenyl-3-butenoate (Formula I, R=phenyl, R$^1$=methyl).

EXAMPLE 3

(Precursor, method ii)

Under nitrogen, 6 ml of hexamethylphosphoramide was added to a stirred solution of 4 g (20 millimole) potassium hexamethyldisilazide in 30 ml tetrahydrofuran. The mixture was cooled to −70° C. and a solution of 3.2 g (20 millimole) ethyl 2-chloro-3-methyl-3-butenoate in 5 ml tetrahydrofuran was added. The deep orange solution was stirred at −70° C. for 20 minutes and 1.2 equivalents of methyl iodide in 2 ml tetrahydrofuran was added rapidly. The mixture was stirred −70° C. for another 15 minutes and then warmed to room temperature. The resulting yellow suspension was then quenched with 10 ml aqueous ammonium chloride and, after 15 minutes, diluted with 50 ml ether. The ether layer was washed with water (2×10 ml), 1N HCl (2×10 ml), 5% NaCl (10 ml), and dried over MgSO$_4$. Evaporation of the solvent yielded the crude product which was further purified by flash column chromatography prior to identification by $^1$H NMR, $^{13}$C NMR, and elemental analysis as ethyl 2-chloro-2,3-dimethyl-3-butenoate (Formula I, R=CH$_3$, R$^1$=CH$_3$).

EXAMPLE 4

(Precursor, method ii)

Generally following the procedure of Example 3, ethyl--chloro-3-methyl-3-butenoate was reacted with the following alkyl halides to produce the ester of Formula I in which R is CH$_3$ and R$^1$ is the alkyl moiety of the alkyl halide.

C$_6$H$_5$—CH$_2$—Br;  a

CH$_2$=CH—CH$_2$—Br;  b $$CH_3-\underset{\underset{CH_3}{|}}{C}=CH-CH_2-Br;$$  c.

CH$_3$—(CH$_2$)$_4$—I;  d

CH$_3$—CH$_2$—CH=CH—CH$_2$—Br.  e

EXAMPLE 5

(Precursor, method ii)

Generally following the procedure of Example 3, ethyl 2-chloro-3-methyl-3-butenoate was reacted with 2-cispentenyl-1-tosylate $$CH_3-CH_2-CH=CH-CH_2-O-\underset{\underset{O}{\|}}{\overset{\overset{O}{\|}}{S}}-C_6H_5$$

to produce ethyl 2-chloro-2-(2-cis-pentenyl)-3-methyl-3butenoate.

EXAMPLE 6

(Invention)

0.80 g (4.4 millimole) of an unsaturated ester of the formula:

$$H_2C=\underset{\underset{Cl}{|}}{\overset{\overset{R}{|}}{C}}-\overset{\overset{R^1}{|}}{C}-\overset{\overset{O}{\|}}{C}-O-C_2H_5$$

in which R and R$^1$ were both methyl (ethyl 2-chloro-2,3-dimethyl-3-butenoate) was mixed with 1 ml toluene and 1.1 g (3 equivalents) of benzyl amine was added. The cloudy mixture was stirred for 1 hour at room temperature and then heated to 70° C. for 2 hours. A yellow cake formed which was diluted with 20 ml of ether and filtered. The ether was evaporated from the yellow filtrate to give 1.1 g of a viscous yellow oil.

The product was further purified by flash column chromatography and its structure identified by $^1$H NMR, $^{13}$C NMR, and mass spectrum analysis as in which R and R$^1$ are each methyl,(N-benzyl-3,4-dimethyl-3-azoline-2-one).

EXAMPLE 7

(Invention)

Generally following the procedures of Example 6, 0.80 g (4.4. millimole) of an unsaturated ester of the structure in Example 6 wherein R is phenyl and R$^1$ is H (ethyl 2-chloro-3-phenyl-3-butenoate) and 1 ml (3 equivalents) of benzyl amine were reacted in 0.5 ml of benzene. A yellow cake and 0.6 g of a thick white precipitate were formed. The white precipitate was stirred with 20 ml of water and filtered to yield 0.3 g of a white powder.

This was washed with hexane and air dried to yield the desired product. The yellow cake was diluted with 20 ml of ether and filtered. The yellow filtrate was evaporated to yield a viscous yellow paste. Flash column chromatography separated the desired product and the total yield was 0.65 g (68%). The structure was identified as the cyclic structure of Example 6 wherein R is phenyl and R$^1$ is H,(N-benzyl-4-phenyl-3-azoline-2-one).

EXAMPLE 8

(Invention)

Generally following the procedures of the preceding examples, ethyl 2-methyl-2-chloro-3-phenyl-3-butenoate (R=phenyl, R$^1$=methyl) was reacted with benzylamine to yield N-benzyl-3-methyl-4-phenyl-3-azoline-2-one (R=phenyl, R$^1$=methyl).

What is claimed is:

1. A method of synthesizing an N,3,4-trisubstituted-3-azoline-2-one of the formula:

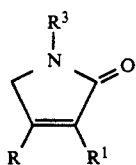

in which R, $R^1$, and $R^3$ are each independently H; a $C_1$–$C_{32}$ alkyl radical; or a $C_1$–$C_{32}$ aryl radical, comprising reacting together under cyclizing conditions a. an ester of the formula:

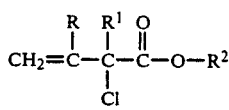

wherein R and $R^1$ are as defined above, and $R^2$ is a $C_1$–$C_{16}$ alkyl radical; with b. a primary amine of the formula:

wherein $R^3$ is as defined above.

2. The method of claim 1 wherein R is methyl or phenyl and $R^1$ is H or methyl.

3. The method of claim 1 wherein $R^3$ is benzyl.

4. The method of claim 1 wherein the reaction takes place in a solvent.

5. The method of claim 1 wherein the reaction takes place at 0° C. to 120° C.

6. A method of synthesizing N-benzyl-4-phenyl-3-azoline-2-one by reacting together under cyclizing conditions ethyl 2-chloro-3-phenyl-3butenoate with benzyl amine to produce said ketone.

7. The method of claim 6 wherein the reaction takes place in a solvent.

8. The method of claim 7 wherein the reaction takes place at a temperature of 0° C.–120° C.

9. A method of synthesizing N-benzyl-3-methyl-4-phenyl-3-azoline-2-one by reaction together under cyclizing conditions ethyl 2-methyl-2-chloro-3-phenyl-3-butenoate with benzylamine to produce said ketone.

10. The method of claim 9 wherein the reaction takes place in a solvent.

11. The method of claim 10 wherein the reaction takes place at a temperature of 0° C. to 120° C.

12. A method of synthesizing N-benzyl-3,4-dimethyl-3-azoline-2-one by reacting under cyclizing conditions ethyl 2-chloro-2,3-dimethyl-3-butenoate with benzyl amine to produce said ketone.

13. The method of claim 12 wherein the reaction takes place in a solvent.

14. The method of claim 13 wherein the reaction takes place at a temperature of 0° C. to 120° C.

* * * * *